United States Patent [19]
Miyoshi et al.

[11] Patent Number: 6,153,433
[45] Date of Patent: *Nov. 28, 2000

[54] INHIBITOR FOR VIRAL REPLICATION

[75] Inventors: Eiji Miyoshi, Osaka; Yoshito Ihara, Mino; Naoyuki Taniguchi, Toyonaka, all of Japan

[73] Assignee: Takara Shuzo Co., Ltd., Kyoto, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/849,281

[22] PCT Filed: Jul. 17, 1996

[86] PCT No.: PCT/JP96/01986

§ 371 Date: May 30, 1997

§ 102(e) Date: May 30, 1997

[87] PCT Pub. No.: WO97/18836

PCT Pub. Date: May 29, 1997

[30] Foreign Application Priority Data

Nov. 17, 1995 [JP] Japan ................................. 7-322474

[51] Int. Cl.⁷ ............................ C12N 15/68; C12N 15/00; C12N 5/00
[52] U.S. Cl. .......................... 435/455; 435/440; 435/456; 435/458; 435/325; 435/320.1; 536/23.1; 536/23.5
[58] Field of Search ....................... 514/2, 44; 435/320.1, 435/325, 440, 455, 456, 458; 530/350; 536/23.1, 23.5

[56] References Cited

U.S. PATENT DOCUMENTS 5,874,271  2/1999  Nishikawa et al. .................... 435/193

FOREIGN PATENT DOCUMENTS 0 585 083  3/1994  European Pat. Off. .
6-38767   2/1994  Japan .

OTHER PUBLICATIONS

Orkin et al. Report and Recommendations of the Panel to Assess the NIH Investment in Research on Gene Therapy. Distributed by the National Institutes of Health, Bethesda, MD. Downloaded from www.nih.gov, Dec. 7, 1995.
Proc. Natl. Acad. Sci. USA, 91, 2235–2239 (1994).
Biochem. and Biophys. Res. Comm., 152(1), 107–112(1988).
Clinica Chimica Acta, 185, 325–332(1989).
Biochimica et Biophysica Acta, 1035(3), 313–318 (1990).
J. Biochem., 113, 692–698 (1993).
J. Biol. Chem., 267(25), 18199–18204 (1992).
Proc. Natl. Acad. Sci. USA, 84, 444–448 (1987).
Cancer Res., 54, 1854–1858 (1994).
J. Biol. Chem., 270(47), 28311–28315 (1995).

*Primary Examiner*—Deborah J. R. Clark
*Attorney, Agent, or Firm*—Wenderoth, Lind & Ponack L.L.P.

[57] ABSTRACT

A pharmaceutical agent which inhibits a replication of virus by increasing the specific enzymatic activity of liver and/or other tissue is offered.

A viral replication inhibitor which contains N-acetyl-glucosaminyltransferase III (GnT-III) or gene thereof as an effective component. Examples of the gene are that which contains a sequence represented by SEQ ID NO:1 (length: 1,608) or by SEQ ID NO:2 (length: 1,593) in the Sequence List, that which is prepared by hybridization of it and codes for a polypeptide having a GnT-III activity or a functionally same activity and that in which the above is further integrated in vector.

14 Claims, 2 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1608 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:1:

```
ATG AGA CGC TAC AAG CTT TTT CTC ATG TTC TGT ATG GCC GGC CTG            45
Met Arg Arg Tyr Lys Leu Phe Leu Met Phe Cys Met Ala Gly Leu
 1               5                  10                  15

TGC CTC ATC TCC TTC CTG CAC TTC TTT AAG ACG TTA TCC TAT GTC            90
Cys Leu Ile Ser Phe Leu His Phe Phe Lys Thr Leu Ser Tyr Val
                20                  25                  30

ACC TTC CCG AGA GAA CTG GCC TCC CTC AGC CCT AAC CTC ATA TCC           135
Thr Phe Pro Arg Glu Leu Ala Ser Leu Ser Pro Asn Leu Ile Ser
                35                  40                  45

AGC TTC TTC TGG AAC AAT GCC CCT GTC ACT CCC CAG GCC AGT CCG           180
Ser Phe Phe Trp Asn Asn Ala Pro Val Thr Pro Gln Ala Ser Pro
                50                  55                  60

GAG CCC GGT GAC CCC GAC TTG TTA CGG ACT CCA CTC TAC TCC CAC           225
Glu Pro Gly Asp Pro Asp Leu Leu Arg Thr Pro Leu Tyr Ser His
                65                  70                  75

TCC CCC CTG CTC CAG CCA CTG TCC CCT AGC AAG GCC ACC GAA GAA           270
Ser Pro Leu Leu Gln Pro Leu Ser Pro Ser Lys Ala Thr Glu Glu
                80                  85                  90

CTG CAC CGG GTG GAC TTC GTG TTG CCG GAG GAC ACC ACA GAG TAT           315
Leu His Arg Val Asp Phe Val Leu Pro Glu Asp Thr Thr Glu Tyr
                95                 100                 105

TTT GTG CGC ACC AAA GCT GGC GGT GTG TGC TTC AAA CCA GGT ACC           360
Phe Val Arg Thr Lys Ala Gly Gly Val Cys Phe Lys Pro Gly Thr
               110                 115                 120

AGG ATG CTG GAG AAA CCT TCT CCA GGG CGG ACA GAG GAG AAG ACC           405
Arg Met Leu Glu Lys Pro Ser Pro Gly Arg Thr Glu Glu Lys Thr
               125                 130                 135

AAG GTG GCT GAG GGG TCC TCG GTC CGG GGT CCT GCT CGG AGG CCT           450
Lys Val Ala Glu Gly Ser Ser Val Arg Gly Pro Ala Arg Arg Pro
               140                 145                 150

ATG CGG CAT GTG TTG AGT GCA CGG GAG CGC CTG GGA GGC CGG GGC           495
Met Arg His Val Leu Ser Ala Arg Glu Arg Leu Gly Gly Arg Gly
               155                 160                 165

ACT AGG CGC AAG TGG GTT GAG TGT GTG TGC CTG CCA GGC TGG CAC           540
```

-continued

```
                Thr Arg Arg Lys Trp Val Glu Cys Val Cys Leu Pro Gly Trp His
                                170                 175                 180

GGG CCC AGC TGC GGG GTG CCC ACT GTG GTC CAG TAT TCC AAC CTG              585
Gly Pro Ser Cys Gly Val Pro Thr Val Val Gln Tyr Ser Asn Leu
                185                 190                 195

CCC ACC AAG GAG CGC CTG GTA CCC AGG GAG GTG CCG AGG CGG GTT              630
Pro Thr Lys Glu Arg Leu Val Pro Arg Glu Val Pro Arg Arg Val
                200                 205                 210

ATC AAC GCC ATC AAC ATC AAC CAT GAG TTC GAC CTG CTG GAT GTG              675
Ile Asn Ala Ile Asn Ile Asn His Glu Phe Asp Leu Leu Asp Val
                215                 220                 225

CGC TTC CAT GAG CTG GGC GAT GTT GTG GAC GCC TTT GTG GTC TGC              720
Arg Phe His Glu Leu Gly Asp Val Val Asp Ala Phe Val Val Cys
                230                 235                 240

GAA TCC AAT TTC ACC GCC TAC GGG GAG CCT CGG CCG CTC AAG TTC              765
Glu Ser Asn Phe Thr Ala Tyr Gly Glu Pro Arg Pro Leu Lys Phe
                245                 250                 255

CGA GAG ATG CTG ACC AAT GGC ACC TTC GAG TAC ATC CGC CAC AAG              810
Arg Glu Met Leu Thr Asn Gly Thr Phe Glu Tyr Ile Arg His Lys
                260                 265                 270

GTG CTC TAC GTC TTC CTG GAC CAC TTC CCA CCT GGT GGC CGT CAG              855
Val Leu Tyr Val Phe Leu Asp His Phe Pro Pro Gly Gly Arg Gln
                275                 280                 285

GAC GGC TGG ATT GCA GAC GAC TAC CTG CGT ACC TTC CTC ACC CAG              900
Asp Gly Trp Ile Ala Asp Asp Tyr Leu Arg Thr Phe Leu Thr Gln
                290                 295                 300

GAT GGT GTC TCC CGC CTG CGC AAC CTG CGA CCT GAT GAC GTC TTT              945
Asp Gly Val Ser Arg Leu Arg Asn Leu Arg Pro Asp Asp Val Phe
                305                 310                 315

ATC ATC GAC GAC GCG GAC GAG ATC CCT GCG CGT GAT GGT GTG CTG              990
Ile Ile Asp Asp Ala Asp Glu Ile Pro Ala Arg Asp Gly Val Leu
                320                 325                 330

TTC CTC AAG CTC TAC GAT GGC TGG ACA GAG CCC TTC GCC TTC CAT             1035
Phe Leu Lys Leu Tyr Asp Gly Trp Thr Glu Pro Phe Ala Phe His
                335                 340                 345

ATG CGC AAG TCC CTG TAT GGT TTC TTT TGG AAG CAA CCA GGC ACA             1080
Met Arg Lys Ser Leu Tyr Gly Phe Phe Trp Lys Gln Pro Gly Thr
                350                 355                 360

CTG GAG GTG GTG TCA GGC TGC ACC ATT GAC ATG CTG CAG GCT GTG             1125
Leu Glu Val Val Ser Gly Cys Thr Ile Asp Met Leu Gln Ala Val
                365                 370                 375

TAT GGG CTG GAC GGC ATC CGC CTG CGC CGC CGT CAG TAC TAC ACC             1170
Tyr Gly Leu Asp Gly Ile Arg Leu Arg Arg Arg Gln Tyr Tyr Thr
                380                 385                 390

ATG CCC AAC TTT CGA CAG TAT GAG AAC CGC ACC GGC CAC ATC CTA             1215
Met Pro Asn Phe Arg Gln Tyr Glu Asn Arg Thr Gly His Ile Leu
                395                 400                 405

GTG CAG TGG TCT CTC GGC AGC CCC CTG CAC TTC GCG GGC TGG CAC             1260
Val Gln Trp Ser Leu Gly Ser Pro Leu His Phe Ala Gly Trp His
                410                 415                 420

TGC TCC TGG TGC TTC ACA CCC GAG GGC ATC TAC TTC AAA CTC GTG             1305
Cys Ser Trp Cys Phe Thr Pro Glu Gly Ile Tyr Phe Lys Leu Val
                425                 430                 435

TCG GCC CAG AAT GGT GAC TTC CCC CGC TGG GGT GAC TAC GAG GAC             1350
Ser Ala Gln Asn Gly Asp Phe Pro Arg Trp Gly Asp Tyr Glu Asp
                440                 445                 450

AAG AGG GAC CTC AAT TAC ATC CGA AGC TTG ATT CGC ACT GGG GGA             1395
Lys Arg Asp Leu Asn Tyr Ile Arg Ser Leu Ile Arg Thr Gly Gly
                455                 460                 465
```

-continued

```
TGG TTC GAC GGC ACG CAG CAG GAG TAC CCT CCT GCA GAC CCC AGT        1440
Trp Phe Asp Gly Thr Gln Gln Glu Tyr Pro Pro Ala Asp Pro Ser
                470                 475                 480

GAA CAC ATG TAT GCT CCT AAG TAC CTG CTC AAG AAC TAT GAC CAG        1485
Glu His Met Tyr Ala Pro Lys Tyr Leu Leu Lys Asn Tyr Asp Gln
            485                 490                 495

TTC CGC TAC TTG CTC GAA AAT CCC TAC CGG GAG CCC AAG AGC ACT        1530
Phe Arg Tyr Leu Leu Glu Asn Pro Tyr Arg Glu Pro Lys Ser Thr
            500                 505                 510

GTA GAG GGT GGG CGC CGG AAC CAG GGC TCA GAC GGA AGG TCA TCT        1575
Val Glu Gly Gly Arg Arg Asn Gln Gly Ser Asp Gly Arg Ser Ser
            515                 520                 525

GCT GTC AGG GGC AAG TTG GAT ACA ACG GAG GGC                        1608
Ala Val Arg Gly Lys Leu Asp Thr Thr Glu Gly
            530                 535
```

(2) INFORMATION FOR SEQ ID NO:2:

(i) SEQUENCE CHARACTERISTICS:
        (A) LENGTH: 1593 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:2:

```
ATG AGA CGC TAC AAG CTC TTT CTC ATG TTC TGT ATG GCC GGC CTG         45
Met Arg Arg Tyr Lys Leu Phe Leu Met Phe Cys Met Ala Gly Leu
  1                 5                  10                 15

TGC CTC ATC TCC TTC CTG CAC TTC TTC AAG ACC CTG TCC TAT GTC         90
Cys Leu Ile Ser Phe Leu His Phe Phe Lys Thr Leu Ser Tyr Val
                20                  25                 30

ACC TTC CCC CGA GAA CTG GCC TCC CTC AGC CCT AAC CTG GTG TCC        135
Thr Phe Pro Arg Glu Leu Ala Ser Leu Ser Pro Asn Leu Val Ser
                 35                  40                 45

AGC TTT TTC TGG AAC AAT GCC CCG GTC ACG CCC CAG GCC AGC CCC        180
Ser Phe Phe Trp Asn Asn Ala Pro Val Thr Pro Gln Ala Ser Pro
                 50                  55                 60

GAG CCA GGA GGC CCT GAC CTG CTG CGT ACC CCA CTC TAC TCC CAC        225
Glu Pro Gly Gly Pro Asp Leu Leu Arg Thr Pro Leu Tyr Ser His
                 65                  70                 75

TCG CCC CTG CTG CAG CCG CTG CCG CCC AGC AAG GCG GCC GAG GAG        270
Ser Pro Leu Leu Gln Pro Leu Pro Pro Ser Lys Ala Ala Glu Glu
                 80                  85                 90

CTC CAC CGG GTG GAC TTG GTG CTG CCC GAG GAC ACC ACC GAG TAT        315
Leu His Arg Val Asp Leu Val Leu Pro Glu Asp Thr Thr Glu Tyr
                 95                 100                105

TTC GTG CGC ACC AAG GCC GGC GGC GTC TGC TTC AAA CCC GGC ACC        360
Phe Val Arg Thr Lys Ala Gly Gly Val Cys Phe Lys Pro Gly Thr
                110                 115                120

AAG ATG CTG GAG AGG CCG CCC CCG GGA CGG CCG GAG GAG AAG CCT        405
Lys Met Leu Glu Arg Pro Pro Pro Gly Arg Pro Glu Glu Lys Pro
                125                 130                135

GAG GGG GCC AAC GGC TCC TCG GCC CGG CGG CCA CCC CGG TAC CTC        450
Glu Gly Ala Asn Gly Ser Ser Ala Arg Arg Pro Pro Arg Tyr Leu
                140                 145                150

CTG AGC GCC CGG GAG CGC ACG GGG GGC CGA GGC GCC CGG CGC AAG        495
Leu Ser Ala Arg Glu Arg Thr Gly Gly Arg Gly Ala Arg Arg Lys
                155                 160                165

TGG GTG GAG TGC GTG TGC CTG CCC GGC TGG CAC GGA CCC AGC TGC        540
Trp Val Glu Cys Val Cys Leu Pro Gly Trp His Gly Pro Ser Cys
```

```
                    170                 175                 180
GGC GTG CCC ACT GTG GTG CAG TAC TCC AAC CTG CCC ACC AAG GAG       585
Gly Val Pro Thr Val Val Gln Tyr Ser Asn Leu Pro Thr Lys Glu
                185                 190                 195

CGG CTG GTG CCC AGG GAG GTG CCG CGC CGC GTC ATC AAC GCC ATC       630
Arg Leu Val Pro Arg Glu Val Pro Arg Arg Val Ile Asn Ala Ile
                200                 205                 210

AAC GTC AAC CAC GAG TTC GAC CTG CTG GAC GTG CGC TTC CAC GAG       675
Asn Val Asn His Glu Phe Asp Leu Leu Asp Val Arg Phe His Glu
                215                 220                 225

CTG GGC GAC GTG GTG GAC GCC TTT GTG GTG TGC GAG TCC AAC TTC       720
Leu Gly Asp Val Val Asp Ala Phe Val Val Cys Glu Ser Asn Phe
                230                 235                 240

ACG GCT TAT GGG GAG CCG CGG CCG CTC AAG TTC CGG GAG ATG CTG       765
Thr Ala Tyr Gly Glu Pro Arg Pro Leu Lys Phe Arg Glu Met Leu
                245                 250                 255

ACC AAT GGC ACC TTC GAG TAC ATC CGC CAC AAG GTG CTC TAT GTC       810
Thr Asn Gly Thr Phe Glu Tyr Ile Arg His Lys Val Leu Tyr Val
                260                 265                 270

TTC CTG GAC CAC TTC CCG CCC GGC GGC CGG CAG GAC GGC TGG ATC       855
Phe Leu Asp His Phe Pro Pro Gly Gly Arg Gln Asp Gly Trp Ile
                275                 280                 285

GCC GAC GAC TAC CTG CGC ACC TTC CTC ACC CAG GAC GGC GTC TCG       900
Ala Asp Asp Tyr Leu Arg Thr Phe Leu Thr Gln Asp Gly Val Ser
                290                 295                 300

CGG CTG CGC AAC CTG CGG CCC GAC GAC GTC TTC ATC ATT GAC GAT       945
Arg Leu Arg Asn Leu Arg Pro Asp Asp Val Phe Ile Ile Asp Asp
                305                 310                 315

GCG GAC GAG ATC CCG GCC CGT GAC GGC GTC CTT TTC CTC AAG CTC       990
Ala Asp Glu Ile Pro Ala Arg Asp Gly Val Leu Phe Leu Lys Leu
                320                 325                 330

TAC GAT GGC TGG ACC GAG CCC TTC GCC TTC CAC ATG CGC ACG TCG      1035
Tyr Asp Gly Trp Thr Glu Pro Phe Ala Phe His Met Arg Thr Ser
                335                 340                 345

CTC TAC GGC TTC TTC TGG AAG CAG CCG GGC ACC CTG GAG GTG GTG      1080
Leu Tyr Gly Phe Phe Trp Lys Gln Pro Gly Thr Leu Glu Val Val
                350                 355                 360

TCA GGC TGC ACG GTG GAC ATG CTG CAG GCA GTG TAT GGG CTG GAC      1125
Ser Gly Cys Thr Val Asp Met Leu Gln Ala Val Tyr Gly Leu Asp
                365                 370                 375

GGC ATC CGC CTG CGC CGC CGC CAG TAC TAC ACC ATG CCC AAC TTC      1170
Gly Ile Arg Leu Arg Arg Arg Gln Tyr Tyr Thr Met Pro Asn Phe
                380                 385                 390

AGA CAG TAT GAG AAC CGC ACC GGC CAC ATC CTG GTG CAG TGG TCG      1215
Arg Gln Tyr Glu Asn Arg Thr Gly His Ile Leu Val Gln Trp Ser
                395                 400                 405

CTG GGC AGC CCC CTG CAC TTC GCC GGC TGG CAC TGC TCC TGG TGC      1260
Leu Gly Ser Pro Leu His Phe Ala Gly Trp His Cys Ser Trp Cys
                410                 415                 420

TTC ACG CCC GAG GGC ATC TAC TTC AAG CTC GTG TCC GCC CAG AAT      1305
Phe Thr Pro Glu Gly Ile Tyr Phe Lys Leu Val Ser Ala Gln Asn
                425                 430                 435

GGC GAC TTC CCA CGC TGG GGT GAC TAC GAG GAC AAG CGG GAC CTG      1350
Gly Asp Phe Pro Arg Trp Gly Asp Tyr Glu Asp Lys Arg Asp Leu
                440                 445                 450

AAC TAC ATC CGC GGC CTG ATC CGC ACC GGG GGC TGG TTC GAC GGC      1395
Asn Tyr Ile Arg Gly Leu Ile Arg Thr Gly Gly Trp Phe Asp Gly
                455                 460                 465

ACG CAG CAG GAG TAC CCG CCT GCA GAC CCC AGC GAG CAC ATG TAT      1440
```

```
Thr Gln Gln Glu Tyr Pro Pro Ala Asp Pro Ser Glu His Met Tyr
            470                 475                 480

GCG CCC AAG TAC CTG CTG AAG AAC TAC GAC CGG TTC CAC TAC CTG      1485
Ala Pro Lys Tyr Leu Leu Lys Asn Tyr Asp Arg Phe His Tyr Leu
            485                 490                 495

CTG GAC AAC CCC TAC CAG GAG CCC AGG AGC ACG GCG GCG GGC GGG      1530
Leu Asp Asn Pro Tyr Gln Glu Pro Arg Ser Thr Ala Ala Gly Gly
            500                 505                 510

TGG CGC CAC AGG GGT CCC GAG GGA AGG CCG CCC GCC CGG GGC AAA      1575
Trp Arg His Arg Gly Pro Glu Gly Arg Pro Pro Ala Arg Gly Lys
            515                 520                 525

CTG GAC GAG GCG GAA GTC                                           1593
Leu Asp Glu Ala Glu Val
            530

(2) INFORMATION FOR SEQ ID NO:3:

(i) SEQUENCE CHARACTERISTICS:
        (A) LENGTH: 536 amino acid residues
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:3:

Met Arg Arg Tyr Lys Leu Phe Leu Met Phe Cys Met Ala Gly Leu
  1               5                  10                  15

Cys Leu Ile Ser Phe Leu His Phe Phe Lys Thr Leu Ser Tyr Val
                 20                  25                  30

Thr Phe Pro Arg Glu Leu Ala Ser Leu Ser Pro Asn Leu Ile Ser
                 35                  40                  45

Ser Phe Phe Trp Asn Asn Ala Pro Val Thr Pro Gln Ala Ser Pro
                 50                  55                  60

Glu Pro Gly Asp Pro Asp Leu Leu Arg Thr Pro Leu Tyr Ser His
                 65                  70                  75

Ser Pro Leu Leu Gln Pro Leu Ser Pro Ser Lys Ala Thr Glu Glu
                 80                  85                  90

Leu His Arg Val Asp Phe Val Leu Pro Glu Asp Thr Thr Glu Tyr
                 95                 100                 105

Phe Val Arg Thr Lys Ala Gly Gly Val Cys Phe Lys Pro Gly Thr
                110                 115                 120

Arg Met Leu Glu Lys Pro Ser Pro Gly Arg Thr Glu Glu Lys Thr
                125                 130                 135

Lys Val Ala Glu Gly Ser Ser Val Arg Gly Pro Ala Arg Arg Pro
                140                 145                 150

Met Arg His Val Leu Ser Ala Arg Glu Arg Leu Gly Gly Arg Gly
                155                 160                 165

Thr Arg Arg Lys Trp Val Glu Cys Val Cys Leu Pro Gly Trp His
                170                 175                 180

Gly Pro Ser Cys Gly Val Pro Thr Val Val Gln Tyr Ser Asn Leu
                185                 190                 195

Pro Thr Lys Glu Arg Leu Val Pro Arg Glu Val Pro Arg Arg Val
                200                 205                 210

Ile Asn Ala Ile Asn Ile Asn His Glu Phe Asp Leu Leu Asp Val
                215                 220                 225

Arg Phe His Glu Leu Gly Asp Val Val Asp Ala Phe Val Val Cys
                230                 235                 240
```

```
Glu Ser Asn Phe Thr Ala Tyr Gly Glu Pro Arg Pro Leu Lys Phe
                245                 250                 255

Arg Glu Met Leu Thr Asn Gly Thr Phe Glu Tyr Ile Arg His Lys
                260                 265                 270

Val Leu Tyr Val Phe Leu Asp His Phe Pro Pro Gly Gly Arg Gln
                275                 280                 285

Asp Gly Trp Ile Ala Asp Asp Tyr Leu Arg Thr Phe Leu Thr Gln
                290                 295                 300

Asp Gly Val Ser Arg Leu Arg Asn Leu Arg Pro Asp Asp Val Phe
                305                 310                 315

Ile Ile Asp Asp Ala Asp Glu Ile Pro Ala Arg Asp Gly Val Leu
                320                 325                 330

Phe Leu Lys Leu Tyr Asp Gly Trp Thr Glu Pro Phe Ala Phe His
                335                 340                 345

Met Arg Lys Ser Leu Tyr Gly Phe Phe Trp Lys Gln Pro Gly Thr
                350                 355                 360

Leu Glu Val Val Ser Gly Cys Thr Ile Asp Met Leu Gln Ala Val
                365                 370                 375

Tyr Gly Leu Asp Gly Ile Arg Leu Arg Arg Gln Tyr Tyr Thr
                380                 385                 390

Met Pro Asn Phe Arg Gln Tyr Glu Asn Arg Thr Gly His Ile Leu
                395                 400                 405

Val Gln Trp Ser Leu Gly Ser Pro Leu His Phe Ala Gly Trp His
                410                 415                 420

Cys Ser Trp Cys Phe Thr Pro Glu Gly Ile Tyr Phe Lys Leu Val
                425                 430                 435

Ser Ala Gln Asn Gly Asp Phe Pro Arg Trp Gly Asp Tyr Glu Asp
                440                 445                 450

Lys Arg Asp Leu Asn Tyr Ile Arg Ser Leu Ile Arg Thr Gly Gly
                455                 460                 465

Trp Phe Asp Gly Thr Gln Gln Leu Tyr Pro Pro Ala Asp Pro Ser
                470                 475                 480

Glu His Met Tyr Ala Pro Lys Tyr Leu Leu Lys Asn Tyr Asp Gln
                485                 490                 495

Phe Arg Tyr Leu Leu Glu Asn Pro Tyr Arg Glu Pro Lys Ser Thr
                500                 505                 510

Val Glu Gly Gly Arg Arg Asn Gln Gly Ser Asp Gly Arg Ser Ser
                515                 520                 525

Ala Val Arg Gly Lys Leu Asp Thr Thr Glu Gly
                530                 535

(2) INFORMATION FOR SEQ ID NO:4:

(i) SEQUENCE CHARACTERISTICS:
        (A) LENGTH:  531 amino acid residues
        (B) TYPE:  amino acid
        (C) STRANDEDNESS:  single
        (D) TOPOLOGY:  linear (ii) MOLECULE TYPE:  polypeptide (xi) SEQUENCE DESCRIPTION: SEQ ID NO:4:

Met Arg Arg Tyr Lys Leu Phe Leu Met Phe Cys Met Ala Gly Leu
 1               5                  10                  15

Cys Leu Ile Ser Phe Leu His Phe Phe Lys Thr Leu Ser Tyr Val
                20                  25                  30
```

-continued

```
Thr Phe Pro Arg Glu Leu Ala Ser Leu Ser Pro Asn Leu Val Ser
             35                  40                  45

Ser Phe Phe Trp Asn Asn Ala Pro Val Thr Pro Gln Ala Ser Pro
         50                  55                  60

Glu Pro Gly Gly Pro Asp Leu Leu Arg Thr Pro Leu Tyr Ser His
             65                  70                  75

Ser Pro Leu Leu Gln Pro Leu Pro Pro Ser Lys Ala Ala Glu Glu
             80                  85                  90

Leu His Arg Val Asp Leu Val Leu Pro Glu Asp Thr Thr Glu Tyr
             95                 100                 105

Phe Val Arg Thr Lys Ala Gly Gly Val Cys Phe Lys Pro Gly Thr
            110                 115                 120

Lys Met Leu Glu Arg Pro Pro Gly Arg Pro Glu Glu Lys Pro
            125                 130                 135

Glu Gly Ala Asn Gly Ser Ser Ala Arg Arg Pro Pro Arg Tyr Leu
            140                 145                 150

Leu Ser Ala Arg Glu Arg Thr Gly Gly Arg Gly Ala Arg Arg Lys
            155                 160                 165

Trp Val Glu Cys Val Cys Leu Pro Gly Trp His Gly Pro Ser Cys
            170                 175                 180

Gly Val Pro Thr Val Val Gln Tyr Ser Asn Leu Pro Thr Lys Glu
            185                 190                 195

Arg Leu Val Pro Arg Glu Val Pro Arg Val Ile Asn Ala Ile
            200                 205                 210

Asn Val Asn His Glu Phe Asp Leu Leu Asp Val Arg Phe His Glu
            215                 220                 225

Leu Gly Asp Val Val Asp Ala Phe Val Val Cys Glu Ser Asn Phe
            230                 235                 240

Thr Ala Tyr Gly Glu Pro Arg Pro Leu Lys Phe Arg Glu Met Leu
            245                 250                 255

Thr Asn Gly Thr Phe Glu Tyr Ile Arg His Lys Val Leu Tyr Val
            260                 265                 270

Phe Leu Asp His Phe Pro Pro Gly Gly Arg Gln Asp Gly Trp Ile
            275                 280                 285

Ala Asp Asp Tyr Leu Arg Thr Phe Leu Thr Gln Asp Gly Val Ser
            290                 295                 300

Arg Leu Arg Asn Leu Arg Pro Asp Asp Val Phe Ile Ile Asp Asp
            305                 310                 315

Ala Asp Glu Ile Pro Ala Arg Asp Gly Val Leu Phe Leu Lys Leu
            320                 325                 330

Tyr Asp Gly Trp Thr Glu Pro Phe Ala Phe His Met Arg Thr Ser
            335                 340                 345

Leu Tyr Gly Phe Phe Trp Lys Gln Pro Gly Thr Leu Glu Val Val
            350                 355                 360

Ser Gly Cys Thr Val Asp Met Leu Gln Ala Val Tyr Gly Leu Asp
            365                 370                 375

Gly Ile Arg Leu Arg Arg Gln Tyr Tyr Thr Met Pro Asn Phe
            380                 385                 390

Arg Gln Tyr Glu Asn Arg Thr Gly His Ile Leu Val Gln Trp Ser
            395                 400                 405

Leu Gly Ser Pro Leu His Phe Ala Gly Trp His Cys Ser Trp Cys
            410                 415                 420
```

```
                                            -continued

Phe Thr Pro Glu Gly Ile Tyr Phe Lys Leu Val Ser Ala Gln Asn
                425                 430                 435

Gly Asp Phe Pro Arg Trp Gly Asp Tyr Glu Asp Lys Arg Asp Leu
                440                 445                 450

Asn Tyr Ile Arg Gly Leu Ile Arg Thr Gly Gly Trp Phe Asp Gly
                455                 460                 465

Thr Gln Gln Glu Tyr Pro Pro Ala Asp Pro Ser Glu His Met Tyr
                470                 475                 480

Ala Pro Lys Tyr Leu Leu Lys Asn Tyr Asp Arg Phe His Tyr Leu
                485                 490                 495

Leu Asp Asn Pro Tyr Gln Glu Pro Arg Ser Thr Ala Ala Gly Gly
                500                 505                 510

Trp Arg His Arg Gly Pro Glu Gly Arg Pro Pro Ala Arg Gly Lys
                515                 520                 525

Leu Asp Glu Ala Glu Val
                530
```

INHIBITOR FOR VIRAL REPLICATION

BACKGROUND OF THE INVENTION

1. Field of the Invention

The present invention relates to a pharmaceutical agent which inhibits replication of virus by increasing a specific enzymatic activity of liver and/or other tissues.

2. Description of the Related Art

Virus has glycoproteins and glycolipids in viral membrane. Glycolipids are derived from cell membrane of host cells while the protein part of glycoproteins is a virus-specific gene product. Sugar chains are added to the protein part in the Golgi apparatus of host cells and, in this process, a viral enzymatic system is not used but an enzymatic system of the host cells is used. For example, there is acquired immunodeficiency syndrome (AIDS) which is a disease where a kind of retrovirus called human immunodeficiency virus (HIV) infects mainly on cells in which molecules of CD4 are expressed whereby CD4-positive T cells are significantly decreased and, in infection of HIV, molecules of gp120 which is a virus envelope glycoprotein play an important role. About one half by weight of the gp120 molecules is occupied by sugar chains and there have been various reports on the importance of those sugar chains during the course of infection of HIV. For example, it is reported that the gp120 molecule lacking the sugar chain loses an ability of binding with CD4. It is also reported that syncytia are formed when HIV-infected cells are cultured together with uninfected cells and that addition of molecules of gp120 inhibit said syncytium formation while addition of molecules of gP120 lacking sugar chains does not cause an inhibition. It is further reported that both E1 and E2 which are thought to constitute the envelopes of human hepatitis C virus (HCV) are glycoproteins and both of them have no sialic acid residue at the end of the sugar chain but a few of them have N-acetylglucosamine residue at the end. Accordingly there is a possibility that liver is infected with HCV via asialoglycoprotein receptor on hepatic parenchymal cells or via mannose-binding protein found in hepatic endodermic cells or macrophage. Furthermore, human hepatitis B virus (HBV) has glycoprotein called an HBs antigen on the surface of its particle where said protein has two N-glycans linked type and it is reported that those sugar chains play an important role in each of the steps of viral replication, translocation and secretion.

Up to now, there have been shown several possibilities of antiviral agents where attention is paid on the sugar chains of those viral glycoprotein. For example, it is reported that syncytium forming ability and virus infecting ability disappear in HIV-infected cells which are cultured in the presence of an inhibitor for N-glycan processing enzyme such as tunicamycin. For example, there is a report on the inhibition of secretion of human HBV by N-butyldeoxynojirimycin which is an iminosugar [Proceedings of the National Academy of Sciences of the U.S.A., 91, 2235–2239 (1994)].

However, a treatment by such an N-glycan processing inhibitor disturbs glycosylation of the host cells and, therefore, the sugar chain structure of glycoprotein of the host cells is naturally affected to a great extent and that is never satisfactory in view of safety.

During the course of studies on the structural change of sugar chain on the cell surface, the present inventors succeeded in obtaining N-acetylglucosaminyltransferase III (GnT-III) of rat and human (Japanese Laid-Open Patent Publications Hei-6/38,767 and European Patent No.585083). This enzyme produces the so-called bisecting GlcNAc, i.e. a GlcNAcβ 1-4Manβ 1 structure of N-glycan.

The present inventors have found already that, in an experimental system using LEC rats which give a natural onset of hepatitis and hepatic cancer, activity of N-acetylglucosaminyl-transferase V (GnT-V) and that of GnT-III significantly increase as compared with the use of LFA (a control rat) in the third stage which is a stage of onset of hepatitis and in the fourth stage where cancer tissues are macroscopically observed in liver, respectively. It has been also found that this GnT-III rarely appears in normal liver but, in a chemical carcinogenic process in rat, the activity increases in cancerous site, precancerous change site, cells derived from ascitic cancer, fetal liver, regenerated liver, etc. It has also been disclosed by the present inventors that an expression of enzymes in a serum of a patient who is suffered from hepatitis, hepatocirrhosis, tissue of hepatic cancer, or hepatic diseases thereof is increased. [Biochemical and Biophysical Research Communications, 152, 107–112 (1988); Clinica Chimica Acta, 185, 325–332 (1989)].

As mentioned already, it has been known that the activity of glycosyltransferase changes in virus-infected cells. However, no method in which such a phenomenon is utilized as a site of action whereby replication of virus is inhibited and viral diseases are treated has been developed yet.

As a result, object of the present invention is to offer a pharmaceutical agent in which a specific enzymatic activity in liver and/or other tissue is increased so that replication of virus is inhibited.

SUMMARY OF THE INVENTION

The present invention relates to an inhibitor for viral replication and it is characterized in that GnT-III or its gene is used as an effective component.

The present inventors have conducted an intensive study for a relation between viral infection and glycosyltransferase activity and, as a result, they have unexpectedly found a surprising fact that, when GnT-III in which the degree of progress of stages in hepatic diseases has a positive relationship with an enzymatic activity is introduced into the cells infected with HBV, expression of HBV gene in said cells is inhibited. Based on this finding, the present invention has been achived.

DETAILED DESCRIPTION OF THE INVENTION

Figure 1:
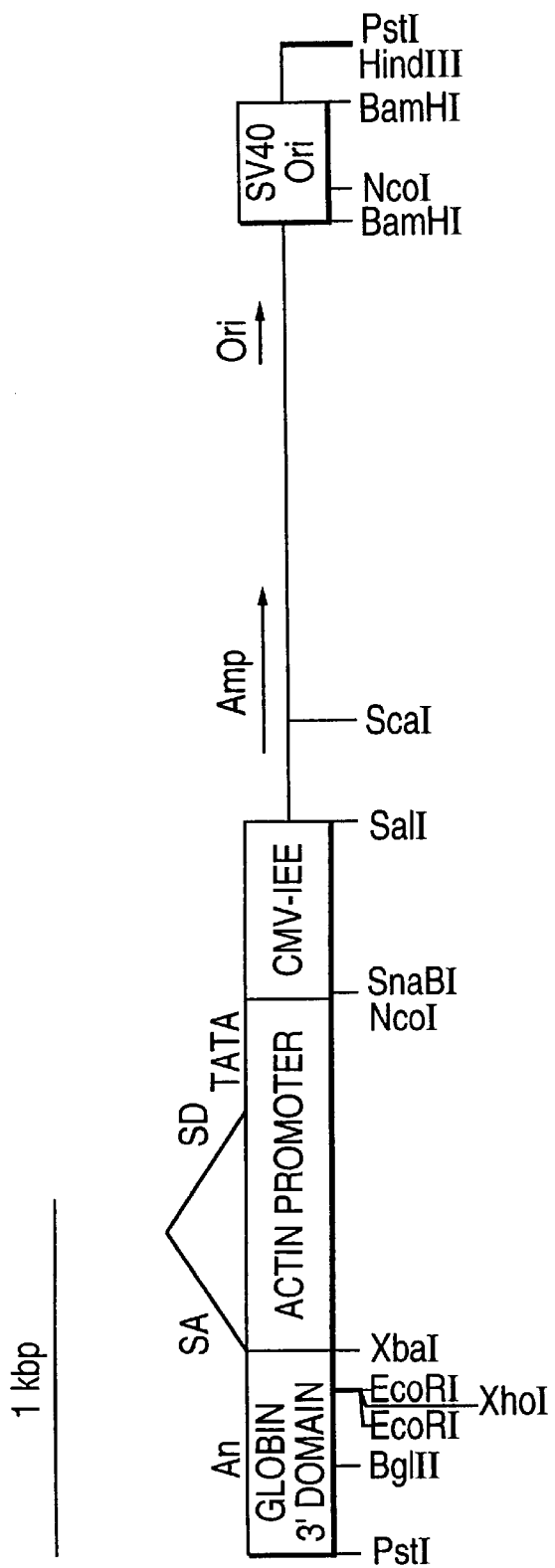
FIG. 1 shows a restriction enzyme map of the pCAGGS vector.

In this specification, a polypeptide having a GnT-III activity covers not only the GnT-III of a natural type but also a polypeptide in which the amino acid sequence of a natural type is modified by deficiency, addition, insertion, substitution, etc. of amino acid residues so far as said polypeptide has a GnT-III activity.

The GnT-III of a natural type referred to hereinabove is exemplified by that which is derived from human or rat although the present invention is not limited thereto but it covers that which is derived from other animals and plants as well as from microorganisms such as bacteria, yeasts, actinomycetes, filamentous fungi, ascomycetes, basidomycetes, etc.

Further, polypeptide having the functionally-same activity as referred to in the present invention means the following.

In the protein which is present in nature, mutations in its amino acid sequence may take place by deficiency, insertion, addition, substitution, etc. of amino acids due to polymorphism and mutation of genes which code for the protein and also due to modification reaction in vivo and in vitro. It is however known that, in spite of the above, there are still certain substances which have substantially same physiological and biological activities as the protein having no modification. Such a substance which differs in terms of structure but has no big difference in terms of function is called a polypeptide having a functionally-same activity.

Even when the mutation as mentioned above is artificially introduced into the amino acid sequence of protein, the same thing occurs as well and, in that case, it is possible to prepare far more varieties of mutants. But, so far as they show the substantially same physiological activity as that which has no mutation, those mutants are still interpreted as the polypeptides having the functionally same activity.

For example, methionine residue existing in an N terminal of protein expressed by Escherichia coli is said to be removed, in many cases, by the action of methionine aminopeptidase but, depending upon the type of the protein, both products with and without the methionine residue are produced. However, there are many cases where the presence or absence of the methionine residue does not affect the activity of the protein. It has been also known that the polypeptide in which certain cysteine residue in the amino acid sequence of human interleukin 2 (IL-2) is substituted with serine maintains an IL-2 activity [Science, 224, 1431 (1984)].

In addition, in the production of protein by means of gene engineering, it is often conducted to express said protein as a fusion protein. For example, it has been conducted in increasing the representation of a desired protein in such a manner that an N terminal peptide chain derived from other protein is added to the N terminal of the desired protein or that N terminal or C terminal of the desired protein is expressed by adding a suitable peptide chain, and a carrier which has an affinity to this added peptide chain is used whereby purification of the desired protein is made easier.

It has been further known that there is/are 1–6 kind(s) of codon (a combination of three bases) specifying an amino acid on the gene for each kind of the amino acids. Accordingly, gene which codes for amino acid sequence may be present in large numbers although that will depend upon the amino acid sequence. In nature, gene is not always present stably and occurrence of mutation in nucleic acid thereof is not rare. In some cases, a mutation which occurred on gene does not give rise to a change to the amino acid sequence to be coded (this is called a silent mutation) and, in that case, it can be said that a different gene coding for the same amino acid sequence was formed. Accordingly, even when a gene which codes for a specific amino acid sequence is isolated, a possibility of formation of many kinds of genes coding for the same amino acid sequence upon a passage of living organisms containing said gene cannot be denied.

Moreover, it is not difficult to artificially prepare many kinds of gene coding for the same amino acid sequence if various gene engineering means are applied.

For example, when the codon used on an inherent gene coding for the desired protein in the production of protein by gene engineering means is that which have low frequency of use among the hosts used, then there are some cases where expression of the protein is low. In such a case, it has been conducted for attempting a high expression of the desired protein that the codon is artificially converted to that which is often used by the host without changing to the coded amino acid sequence. Needless to say, it is possible to artificially prepare the gene which codes for a specific amino acid sequence as such. Accordingly, even such an artificially prepared and different polypeptide is included in the present invention so far as the amino acid sequence disclosed in the present invention is coded therefor.

Further, there is not a few cases where a polypeptide wherein at least one of deficiency, addition, insertion and substitution of one or more amino acid residue(s) is conducted to the amino acid sequence of the desired protein has the functionally same activity to the desired protein. Gene which codes for such a polypeptide is also covered by the present invention independently of being prepared either naturally or artificially.

Usually, there are many cases that, in the case of polypeptides having the functionally same activity, genes coding for them are homologous. Accordingly, the gene which can hybridize with the gene used in the present invention and which codes for a polypeptide having a GnT-III activity is included in the present invention as well.

The present invention will be illustrated in detail as hereunder.

In the present invention, the object can be achieved by introducing GnT-III into the cell infected with HBV. In introducing GnT-III, the GnT-III maintaining its activity may be directly introduced into the cells infected with HBV by, for example, a microinjection method or, alternatively, the GnT-III gene is introduced into the cells infected with HBV using virus or the like to express the GnT-III whereby an object of the present invention can be achieved.

Thus, when the pharmaceutical agent of the present invention is used, GnT-III or the gene which codes for GnT-III can be introduced into virus-infected cells or other tissues whereby replication of the virus can be inhibited. GnT-III or the gene coding for GnT-III may be directly injected into the affected part on the tissue surface. Alternatively, a drug delivery system (DDS) where it can be directly injected into the affected part inside the tissue may be applied too. The DDS may be a system which is specific to virus-infected cells.

When a pharmaceutical agent of the present invention containing GnT-III or gene thereof is applied to virus-infected cells or other tissues, it goes without saying that said pharmaceutical agent is made in such a manner that said agent displays the effect most efficiently.

The virus replication inhibitor in accordance with the present invention may contain GnT-III or gene thereof within a pharmaceutically acceptable range and can be made into pharmaceutical preparations by the same manner as in the case of common gene therapeutic agents and protein-containing agents. The pharmaceutical preparation may contain carriers, fillers, stabilizers, etc.

Dose of GnT-III or gene thereof which is used as a virus replication inhibitor of the present invention may be adjusted by taking the state of the patient such as age and body weight and degree of the affected part into consideration.

GnT-III or gene thereof contained in the virus replication inhibitor of the present invention is an intravital substance and has no toxicity.

With respect to GnT-III which is used in the present invention, its detailed properties have been clarified already and can be prepared, for example, from kidney of rat by the steps as mentioned in Table 1.

TABLE 1

| Steps | Specific Activity (nmole/mg/h) |
|---|---|
| 1. Homogenate | 2.16 |
| 2. Extraction with Tritone | 8.94 |
| 3. QAE-Sepharose | 42.1 |
| 4. Hydroxyappatite | 74.6 |
| 5. $Cu^{2+}$ Chelating Sepharose | 248 |
| 6. ConA Sepharose | 578 |
| 7. $Cu^{2+}$-Chelating Sepharose | 820 |
| 8. UDP-Hexanolamine Agarose | 7,230 |
| 9. Gn,Gn-bi-Asn Sepharose | 331,000 |

[In the above table, Gn,Gn-bi-Asn Sepharose is an abbreviation for GlcNAcβ 1-2Manα 1-6(GlcNAcβ 1-2Manα 1-3) Manβ 1-4GlcNAcβ 1-4GlcNAc-Asn. Activity of GnT-III was measured by a method mentioned in Biochimica et Biophysica Acta, 1035, (3) 313–318 (1990) using 80 µM of a fluorescent substrate while specific activity of the enzyme was expressed in terms of the transferred GlcNAc(mole)/protein(mg)/hour(h) using pyridyl(-2-)aminated GlcNAc as a standard substance. Protein was measured by a BCA kit (manufactured by Pirce) using serum albumin as a standard substance.]

Said gene can be prepared, for example, from human fetal liver cDNA library by a method of Ihara et al [Journal of Biochemistry, 113, 692–698 (1993)]. In addition, the gene which is prepared, for example, from cDNA library of kidney of rat by a method of Nishikawa et al [Journal of Biological Chemistry, 267, 18199–18204 (1992)] can be a suitable experimental material in the study of inhibition of replication of HBV.

Moreover, GnT-III of rat, for example, may be prepared by a method mentioned in the Japanese Laid-Open Patent Publication Hei-6/38,767 using a strain FERM BP-4352 (this strain was named and indicated as *Escherichia coli* XL1-Blue SV3, deposited in the Biotechnology Research Institute, Agency of Industrial Science and Technology, Ministry of International Trade and Industry of Japan [1-3, Higashi-1-chome, Isukuba City, Ibaragi Prefecture, Japan (Post Office Code: 305)] on Jan. 22, 1992 as FERM P-12718 and transferred to an international deposit in accordance with the Treaty of Budapest from the original deposit by the above-mentioned Biotechnology Research Institute, Agency of Industrial Science and Technology, MITI).

Further, with respect to human GnT-III for example, it can be prepared by a method mentioned in the European Patent No. 585083.

In SEQ ID NO:1 and 3 of the Sequence Listing, DNA sequence of the gene coding for GnT-III of rat and amino acid sequence thereof, respectively, are given. In SEQ ID NO:2 and 4 of the Sequence Listing, DNA sequence of the gene coding for human GnT-III and amino acid sequence thereof, respectively, are given. When such a gene is used as probes, it is possible to prepare a gene which hybridizes to said gene and codes for the protein showing a GnT-III activity. It is also possible to prepare a gene which hybridizes to the gene shown by SEQ ID NO.1 or 2 of the Sequence Listing and codes for the protein showing a GnT-III activity by subjecting the gene represented by SEQ ID NO.1 or 2 of the Sequence Listing to gene engineering substitution, mutation, scission and the like.

Such genes and expression proteins of said genes may be used as a pharmaceutical agent of the present invention as well.

When the GnT-III of the pharmaceutical agent of the present invention is introduced into cells using the gene itself, it is possible to easily introduce the GnT-III gene using, for example, a recombinant vector having GnT-III and regulatory gene related thereto. It is of course also possible to use effective promoters other than the promoter for GnT-III itself such as SV40 promoter, retrovirus-derived LTR promoter, heat shock promoter, metallothionein promoter and actin promoter.

In an introduction of the GnT-III gene, vector containing said gene is efficiently introduced into the cells which are or are not infected with HBV using a virus vector whereby an object of the present invention can be achieved. With respect to such a vector, retrovirus and vaccinia virus which have been known to transport the desired DNA to the cell and show a high infection efficiency and, in addition, nonvegetative recombinant virus and the like may be used. Particularly, nonvegetative recombinant has an advantage that, although it is to be used biweekly to bimonthly since the recombinant virus is not propagated after being introduced into the desired cells or the like, its amount can be adjusted at that time. Moreover, liposome which is an artificial lipid capsule may be used too.

With respect to a construction method for the vector which is desirable as a pharmaceutical agent of the present invention, the following method may be used. Thus, cDNA of human GnT-III is introduced into an EcoRI site of the pCAGGS vector supplied by Professor Kenichi Yamamura of Kumamoto University whereby an expression vector of GnT-III controlled by actin promoter can be prepared.

FIG. 1 shows a restriction map of the pCAGGS vector.

With respect to replication of the virus, degree of the replication can be determined by, for example, measuring the amount of HBe antigen or HBs antigen which is an antigen related to the virus produced by the treated cells in a medium. Thus, the DNA which is prepared by a linearization of the above GnT-III expression vector with SalI and another DNA which is prepared by a linearization of pMEP (vector having a hygromycin-resisting genes; manufactured by Invitrogen) with BamHI are mixed and introduced into HB611 cells wherein HBV genome gene is integrated in tandem into the above-mentioned Huh-6 cells [Proceedings of the National Academy of Sciences of the U.S.A., 84, 444–448 (1987)] by means of an electroporation. After that, a culture is conducted in a medium containing hygromycin to screen the resisting cell strains. Several cell strains expressing the GnT-III activity prepared as such are selected and the amount of HBs antigen or HBe antigen is measured.

Measurement of HBs antigen or HBe antigen may be conducted, for example, by means of a radioimmunoassay in accordance with a method as reported by the present inventors [International Journal of Cancer, 52, 137–140 (1992)].

It is also possible to obtain an information on replication of virus by measuring the amount of messenger RNA (mRNA) from virus. Thus, the amount of viral mRNA can be evaluated by a northern blot hybridization using a $^{32}P$-labeled viral cDNA as a probe.

The present inventors have found that the expression level of the HBV-proteins in the GnT-III gene containing HBV-integrated HB611 cells is clearly lower than that of the HBV-proteins in the original HBV-integrated HB611 cells.

The pharmaceutical agent of the present invention is useful in a field in which viral diseases are to be treated.

The present invention will now be further illustrated by way of the following examples although the present invention is not limited to those examples.

EXAMPLE 1

Construction of Expression Vector and its Introduction into Cells cDNA clone C4 containing a whole length of coding region of rat GnT-III [Journal of Biological Chemistry, 267, 18199–18204 (1992)] was digested with EcoRI (manufactured by Takara Shuzo) and cloned in an EcoRI site of pCAGGS vector (provided by Dr. Kenichi Yamamura, Kumamoto University). FIG. 1 shows a restriction map of the pCAGGS vector.

Figure 2:
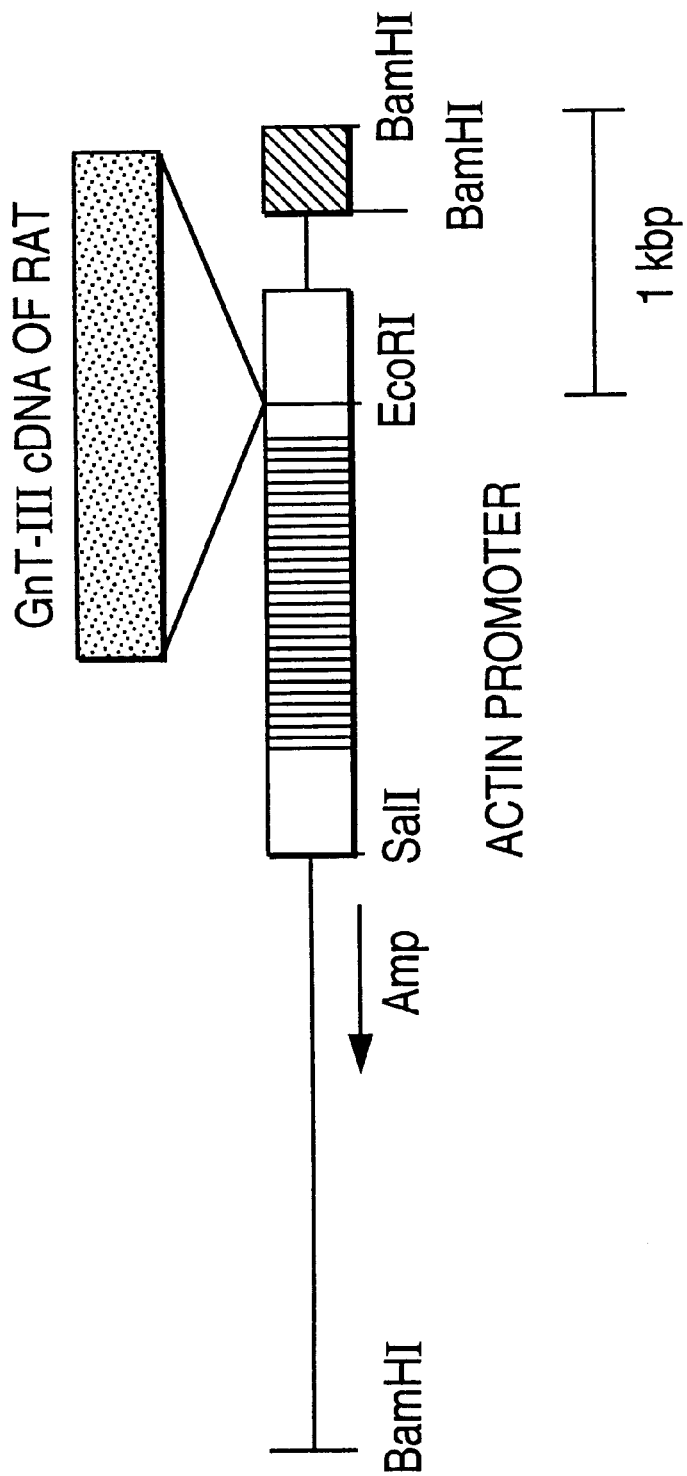
FIG. 2 shows a scheme of GnT-III expressed plasmid Act-5.

The expression plasmid constructed as such was named GnT-III expression plasmid Act-5. In this GnT-III expression plasmid Act-5, expression of GnT-III will be controlled by an actin promoter. FIG. 2 shows a scheme of GnT-III expression plasmid Act-5. In the drawing, a solid bold line on the upper column (in solid black) shows cDNA of the rat GnT-III while the lower column shows pCAGGS vector (FIG. 1). The area with vertical stripes in the lower column shows an actin promoter while that with oblique stripes shows SV40ori.

The GnT-III expression plasmid Act-5 and pMEP vector (manufactured by Invitrogen; a vector having hygromycin-resistance genes) were digested with SalI (manufactured by Takara Shuzo) and BamHI (manufactured by Takara Shuzo), respectively to linearize, then 20 $\mu$g of GnT-III expression plasmid Act-5 and 2 $\mu$g of pMEP vector were mixed and were introduced into $5 \times 10^5$ HB611 cells by means of an electroporation using a Gene Pulser (manufactured by Biorad; voltage: 250 volts/0.4 cm; electrostatic capacity: 960 $\mu$F). Incidentally, the HB611 cell is a cell in which HBV genome gene is introduced into Huh-6 cell derived from human liver blast edema in tandem [Proceedings of the National Academy of Sciences of the U.S.A., 84, 444–448 (1987)] and was provided by Dr. Kenichi Matsubara, Cell Technology Center, Osaka University.

Selection of the gene-introduced cells was conducted in a medium containing hygromycin (500 $\mu$g/ml) and the resisting cell strain was cloned by a dilution method. As a result thereof, three cell strains having a GnT-III activity and three cell strains having no GnT-III activity were obtained. The cells having a GnT-III activity (GnT-III positive cells) were named HB611-GNT-III(1), HB611-GNT-III(2) and HB611-GNT-III(3) while the cells having no GnT-III activity (GnT-III negative cells) were named HB611-hygro(1), HB611-hygro(2) and HB611-hygro(3).

Enzymatic Activity of GnT-III and GnT-V of the Cells

About $5-10 \times 10^6$ cells in a confluent state were collected, washed with a phosphate-buffered physiological saline solution (PBS), suspended in 0.2 ml of the same solution and subjected to an ultrasonication. Each enzymatic activity was measured in such a manner that the resulting ultrasonicated solution subjected to a measurement of the activity of GnT-III, N-acetylglucosaminyl-Transferase IV (GnT-IV) and GnT-V in the cell was measured three times for each cell by a method mentioned in Analytical Biochemistry, 170, 349–354 (1988), Methods in Enzymology, 179, 397–408 (1985) and Journal of Biological Chemistry, 265, 6009–6018 (1990) using an enzyme solution and sugar chain which was subjected to a fluorescent labeling as substrates.

The results are given in Table 2.

TABLE 2

| Cells | GnT-III | GnT-IV | GnT-V |
| --- | --- | --- | --- |
| HB611 | 9.9 ± 3.4 | 143 ± 30 | 163 ± 23 |
| HG611-hygro(1) | 8.2 ± 1.7 | 138 ± 27 | 181 ± 30 |
| HG611-hygro(2) | 17.0 ± 5.1 | 237 ± 32 | 209 ± 22 |
| HG611-hygro(3) | 13.0 ± 2.7 | 117 ± 4.7 | 182 ± 11 |
| HG-611-GNT-III(1) | 98.0 ± 17* | 145 ± 40 | 225 ± 18 |
| HG-611-GNT-III(2) | 103.0 ± 9.2* | 146 ± 28 | 179 ± 18 |
| HG-611-GNT-III(3) | 81.0 ± 9.8* | 122 ± 11 | 200 ± 19 |

In the table, * shows a statistical result which was conducted by means of Student's t-test where $p<0.01$ for HB611 cells. The term $p<0.01$ means that the possibility where the result is same as that to HB611 is less than 0.01.

As shown in Table 2, the GnT-III activity increased to an extent of about 8 to 10-fold of that of parent strains in the case of GnT-III positive cell. Activities of GnT-IV and GnT-V hardly changed between the parent strain and the transformant.

Then the amount of mRNA of GnT-III was subjected to a northern blot hybridization by a method mentioned in "Molecular Cloning, A Laboratory Manual", Second Edition, by T Maniatis, et al., Chapter 7, pages 39–52, published by Cold Spring Harbor Laboratory, 1989. As a result of comparison of the amounts of mRNA of GnT-III in HB611 cells and in six kinds of the cells obtained hereinabove, GnT-III was highly expressed in GnT-III positive cells.

Evaluation of HBV Replication

In order to evaluate the expression of HBV-related protein in HB611 cells, amounts of HBs antigen and HBe antigen in the medium were measured using a Radioimmunoassay Kit (manufactured by Otsuka Assay Kenkyusho) by a method reported by the present inventors already [International Journal of Cancer, 52, 137–140 (1992)]. HB611 cells and the transformant thereof were peeled off from the plate using a PBS containing 0.5 mM of EDTA and the numbers of the cells were measured. The amounts of HBs antigen and HBe antigen were expressed in terms of a relative unit per cell. Incidentally, in the case of the transformants, GnT-III positive cells (HB611-GnT-III) and GnT-III negative cells (HB611-hygro) were used.

The results are given in Table 3.

TABLE 3

| Cells | Amount of HBs Antigen | Amount of HBe Antigen |
| --- | --- | --- |
| HB611 | 30.2 | 108.0 |
| HB611-hygro | 24.0 ± 14.7 | 95.0 ± 12.9 |
| HB611-GNT-III | 4.5 ± 3.3* | 24.4 ± 8.1* |

In the table, * shows a result wherein the statistic treatment was conducted by means of Student's t-test in which $p<0.02$ to HB611-hygro cells.

As shown in Table 3, the amounts of HBs antigen and HBe antigen in the medium of the GnT-III positive cells were clearly decreased as compared with the case of GnT-III negative cells and parent strains.

Then the expression of the HBV-related mRNA was evaluated by a northern blot hybridization using a method mentioned in "Molecular Cloning, A Laboratory Manual, Second Edition, by T. Maniatis et al., Chapter 7, pages 39–52, Cold Spring Harbor Laboratory, 1989 using $^{32}$P- labeled HBV whole cDNA as a probe. Expression of the HBV-related mRNA in the HB611 cells and the above-prepared six kinds of cells were compared in terms of the amounts of HBV, β-actin and ribosome RNA (rRNA) and, as a result, it was found that, in GnT-III positive cells, the expression of HBV-related mRNA was also obviously inhibited as compared with GnT-III negative cells and parent strains.

On the other hand, expressions of the mRNA of alphafetoprotein (AFP), albumin and prealbumin protein in the HB611 cells and in the above-prepared six kinds of cells were measured. As a result, in any of the cells, the expressions of AFP, albumin and prealbumin protein were not related to the level of the GnT-III activity.

In accordance with the present invention, a virus replication inhibitor which is characterized in that said inhibitor containing GnT-III or gene thereof increasing the GnT-III activity of virus-infected cells or other tissues as an effective component is offered. Said virus replication inhibitor is useful in the field of therapy of viral diseases.

What is claimed is:

1. A method of inhibiting the replication of a Hepatitis B virus in vitro comprising introducing in vitro a DNA encoding a polypeptide having the amino acid sequence as set forth in SEQ ID No: 3 or 4, into one or more cells infected with the virus.

2. The method according to claim 1, wherein the DNA comprises the nucleic acid sequence as set forth in SEQ ID NO: 1 or 2.

3. The method according to claim 1, wherein the DNA is integrated into a vector.

4. The method according to claim 3, wherein the vector is a plasmid vector.

5. The method according to claim 3, wherein the vector is a virus vector.

6. The method according to claim 5, wherein the virus vector is a retro-virus vector.

7. The method according to claim 1, wherein the DNA is introduced via a virus or liposome.

8. The method according to claim 1, wherein the DNA is introduced via a retrovirus or vaccinia virus.

9. A method of inhibiting the replication of a Hepatitis B virus in vitro comprising introducing in vitro a composition comprising (1) a DNA encoding a polypeptide having the amino acid sequence as set forth in SEQ ID No: 3 or 4, and (2) a preparation agent selected from the group consisting of a carrier, a filler and a stabilizer, into one or more cells infected with the virus.

10. The method according to claim 9, wherein the DNA comprises the nucleic acid sequence as set forth in SEQ ID No: 1 or 2.

11. The method according to claim 9, wherein the DNA is integrated into a vector.

12. The method according to claim 11, wherein the vector is a plasmid vector.

13. The method according to claim 11, wherein the vector is a virus vector.

14. The method according to claim 13, wherein the virus vector is a retro-virus vector.

* * * * *